(12) United States Patent
Zhang et al.

(10) Patent No.: US 10,188,305 B2
(45) Date of Patent: Jan. 29, 2019

(54) LOCATING J-POINTS IN ELECTROCARDIOGRAM SIGNALS

(71) Applicant: DRÄGERWERK AG & CO. KGAA, Lübeck (DE)

(72) Inventors: Zhe Zhang, Andover, MA (US); Scott Roset, Lowell, MA (US); Yu Chen, Andover, MA (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 141 days.

(21) Appl. No.: 15/199,036

(22) Filed: Jun. 30, 2016

(65) Prior Publication Data

US 2017/0007144 A1    Jan. 12, 2017

Related U.S. Application Data

(60) Provisional application No. 62/190,697, filed on Jul. 9, 2015.

(51) Int. Cl.

| | |
|---|---|
| *A61B 5/0456* | (2006.01) |
| *A61B 5/0468* | (2006.01) |
| *A61B 5/04* | (2006.01) |
| *A61B 5/0408* | (2006.01) |
| *A61B 5/00* | (2006.01) |
| *A61B 5/0452* | (2006.01) |

(52) U.S. Cl.
CPC ........ *A61B 5/04012* (2013.01); *A61B 5/0452* (2013.01); *A61B 5/7282* (2013.01); *A61B 5/04085* (2013.01)

(58) Field of Classification Search
CPC . A61B 5/04012; A61B 5/0452; A61B 5/7282; A61B 5/04085
USPC ........................................................ 600/521
See application file for complete search history.

(56) References Cited

U.S. PATENT DOCUMENTS

| | | |
|---|---|---|
| 6,625,490 B1 | 9/2003 | McClure et al. |
| 6,650,931 B1 | 11/2003 | McClure et al. |
| 7,991,459 B2 | 8/2011 | Palreddy et al. |
| (Continued) | | |

FOREIGN PATENT DOCUMENTS

| | | |
|---|---|---|
| EP | 2537460 A1 | 12/2012 |
| WO | 2014123512 A1 | 8/2014 |
| WO | 2015048514 A1 | 4/2015 |

OTHER PUBLICATIONS

Gowdar, "Automatic detection of QT and related intervals," Thesis, Department of Biomedical Engineering, New Jersey Institute of Technology (2006).
Dasskalov et al., "Developments in ECG Acquisition, Preprocessing, Parameter Measurement, and Recording," IEEE Engineering in Medicine and Biology Magazine, 17(2):50-58 (1998).
(Continued)

*Primary Examiner* — Carl H Layno
*Assistant Examiner* — Erin M Piateski
(74) *Attorney, Agent, or Firm* — Wenderoth, Lind & Ponack, L.L.P.

(57) ABSTRACT

The current subject matter determines the location of the J-point in an ECG signal by examining ECG samples within a window of samples between the S-peak and the T-peak. The sample in this range with the smallest distance, $\Delta d$, to the R-peak is selected as the J-point. Thus, the J-point location can be determined based on an ECG sample's distance to the R-peak. The J-point location can then be used to determine whether there is elevation or depression of the ST segment. Related apparatus, systems, techniques, and articles are also described.

17 Claims, 13 Drawing Sheets

(56) References Cited

U.S. PATENT DOCUMENTS

| | | | |
|---|---|---|---|
| 8,855,752 B2 | 10/2014 | Johnson | |
| 2009/0088655 A1* | 4/2009 | Vajdic | A61B 5/04011 600/523 |
| 2009/0216144 A1 | 8/2009 | Hopenfeld | |
| 2011/0040200 A1 | 2/2011 | Douglas et al. | |
| 2012/0053473 A1* | 3/2012 | Johnson | A61B 5/0006 600/509 |
| 2012/0123283 A1 | 5/2012 | Tikkanen et al. | |
| 2014/0249437 A1 | 9/2014 | Zong et al. | |
| 2014/0275925 A1* | 9/2014 | Thakur | A61B 7/04 600/377 |
| 2014/0276140 A1* | 9/2014 | Kinghorn | A61B 5/0215 600/486 |
| 2015/0011902 A1* | 1/2015 | Wang | A61B 5/044 600/509 |
| 2015/0045681 A1 | 2/2015 | Lee et al. | |
| 2015/0065814 A1* | 3/2015 | Kapoor | A61B 7/00 600/301 |

OTHER PUBLICATIONS

Pan et al., "A Real-Time QRS Detection Algorithm," IEEE Transactions on Biomedical Engineering, BME-32 (3):230-236 (1985).

Papaloukas et al., "A Robust Knowledge-Based Technique for Ischemia Detection in Noisy ECGs," Knowledge-Based Intelligent Engineering Systems and Allied Technologies, 2000. Proceedings. Fourth International Conference on, IEEE, 2:768-771 (2000).

Smrdel et al., "An Algorithm to Estimate the ST Segment Level in 24-Hour Ambulatory ECG Records," Computers in Cardiology, 35:701-704, (2008).

Tompkins, Biomedical Digital Signal Processing. C-Language Examples and Laboratory Experiments for the IBM® PC, Prentice Hall, Upper Saddle River, New Jersey, pp. 1-368 (2000).

Zong et al., "A Real-Time ST-Segment Monitoring Algorithm Based on a Multi-Channel Waveform-Length-Transform Method for Q-Onset and J-Point Detection," Computing in Cardiology Conference (CinC), 41:641-644, (2014).

Zong et al., "A Robust Open-Source Algorithm to Detect Onset and Duration of QRS Complexes," Computers in Cardiology, IEEE, 30:737-740 (2003).

\* cited by examiner

LOCATING J-POINTS IN ELECTROCARDIOGRAM SIGNALS

RELATED APPLICATION

The current application claims priority to U.S. Pat. App. Ser. No. 62/190,697 filed on Jul. 9, 2015, the contents of which are hereby fully incorporated by reference.

TECHNICAL FIELD

The subject matter described herein relates to locating the J-point of an electrocardiogram (ECG) waveform.

BACKGROUND

Electrocardiography is the process of recording the electrical activity of the heart over a period of time using a set of electrodes placed on the body of a patient. These electrodes detect electrical changes on the skin that arise from the heart muscle depolarizing during each heartbeat. In a conventional twelve lead ECG, ten electrodes are placed on the patient's limbs and on the surface of the chest. The overall magnitude of the heart's electrical potential is then measured from twelve different angles ("leads") and is recorded over time. The overall magnitude and direction of the heart's electrical depolarization can be measured at each moment throughout the cardiac cycle. The graph of voltage versus time produced by this noninvasive medical procedure is the electrocardiogram (ECG) waveform.

SUMMARY

In some aspects, the current subject matter determines the location of the J-point in an ECG signal by examining ECG samples between the S-peak and the midpoint between the S-peak and the T-peak. The sample in this range with the smallest distance, $\Delta d$, to the R-peak is selected as the J-point. Thus, the J-point location can be determined based on an ECG sample's distance to the R-peak.

In an interrelated aspect, electrocardiogram (ECG) data derived from an ECG electrode set affixed to a patient is received. The ECG data includes a sequence of cardiac cycle waveforms that each correspond to a single cardiac cycle. In addition, each waveform comprises a series of samples. Subsequently, an R-peak, an S-peak, and a T-peak are located for each cardiac cycle waveform. For each cardiac cycle waveform, a sample within a window of samples between the S-peak and the T-peak that is closest in distance to the R-peak is then identified. Thereafter, for each cardiac cycle waveform, data specifying a location of the identified sample as being a J-point for the corresponding cardiac cycle waveform is provided. Provided can include, for example, displaying at least a portion of the data on an electronic display, loading at least a portion of the data into memory, storing at least a portion of the data into persistent storage, or transmitting at least a portion of the data to a remote computing system.

A midpoint sample between the S-peak and the T-peak can be calculated for each cardiac cycle waveform. With such variations, the window can only includes samples between the S-peak and the midpoint sample.

In some variations, for each cardiac cycle waveform, a beginning of a T wave corresponding to the T-peak can be identified. With such a variation, deviation of an ST segment starting at the J-point and terminating at the beginning of the T wave can be measured relative to a baseline. The ST segment corresponds to an interval between ventricular depolarization and repolarization of the patient. The baseline can be a TP interval of the corresponding cardiac cycle waveform defined by the end of the T wave and start of a next P wave in the cardiac cycle waveform. In addition or in the alternative, the baseline can be a PR interval of the corresponding cardiac cycle waveform defined by an end of a P wave and start of a QRS complex in the cardiac cycle waveform. Data characterizing the measured deviation of the ST segment can be provided (e.g., displayed in an electronic display, loading into memory, stored in persistent storage, or transmitted to a remote computing system).

The measured deviation can be an elevation of the ST segment relative to the baseline or a depression of the ST segment relative to the baseline.

Prior to the calculating, each cardiac cycle waveform can be scaled to a predetermined scale. The scaling can apply equal weights to each axis of the cardiac cycle waveform. At least one cardiac cycle waveform can be scaled such that, on an x-axis of the cardiac cycle waveform, the scaling is between the R-peak and the midpoint sample. At least one cardiac cycle waveform can be scaled such that, on a y-axis of the cardiac cycle waveform, the scaling is between the R-peak and the S-peak.

The identifying can include calculating a distance of each sample between the R-peak and the midpoint sample, wherein the identified sample corresponds to the sample having the shortest distance from the R-peak.

In some variations, the identifying can include calculating a distance of a subset of samples between the R-peak and the midpoint sample, wherein the identified sample corresponds to the sample having the shortest distance from the R-peak. With such a variation, a portion of the samples not forming part of the subset of samples can be skipped such that a distance is not calculated for such sample(s). Selection of samples for which distances can be calculated are based on a characteristic of a sample for which a distance was previously calculated.

The identifying can include calculating, for each sample in sequential temporal order, a distance of the sample from the midpoint R-peak until the midpoint sample is reached such that the identified sample corresponds to the sample having the shortest distance from the R-peak. Alternatively, the identifying can include calculating, for each sample in reverse sequential temporal order starting at the midpoint sample, a distance of the sample from the midpoint R-peak until the R-peak is reached such that the identified sample corresponds to the sample having the shortest distance from the R-peak.

At least one of the receiving, locating, calculating, identifying, or providing can be executed by a patient monitor in communication with the ECG electrode set.

The ECG data can be continuously updated while the patient is being monitored so that the J-point is continuously calculated.

In another variation, a system can include at least one data processor, and memory storing instructions. These instructions, when executed by the at least one data processor, cause the system to perform certain operations. These operations can include receiving electrocardiogram (ECG) data derived from an ECG electrode set affixed to a patient. The ECG data can include a sequence of cardiac cycle waveforms that each correspond to a single cardiac cycle with each waveform comprising a series of samples. The operations can also include locating, for each cardiac cycle waveform, an R-peak, an S-peak, and a T-peak. In addition, the operations can include identifying, for each cardiac cycle waveform, a sample within a window of samples between the S-peak and the T-peak that is closest in distance to the R-peak. Still further, the operations can include providing, for each cardiac cycle waveform, data specifying a location of the identified sample as being a J-point for the corresponding cardiac cycle waveform.

The system can include an electrocardiogram (ECG) electrode set for generating ECG signals when affixed to a patient. In addition, in some variations, the at least one data processor and memory can form part of a patient monitor having an interface for communication with the ECG electrode set.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many technical advantages. For example, the current subject matter can more accurately locate the J-point within a cardiac cycle of an ECG waveform. In addition, ST segment elevation can be accurately measured for detection of myocardial ischemia and infarction in a patient. Further, the current subject matter can be faster computationally and can be influenced less by electronic noise, artifacts, and physiological changes of the patient.

The details of one or more variations of the subject matter described herein are set forth in the accompanying drawings and the description below. Other features and advantages of the subject matter described herein will be apparent from the description and drawings, and from the claims.

DETAILED DESCRIPTION

The current subject matter is directed to the detection of a J-point feature within a cardiac cycle waveform (representing a heartbeat) which, in turn, can be used to measure the elevation of the ST segment of a cardiac cycle waveform to detect myocardial ischemia and infarction in a patient. Conventional algorithms for locating the J-point may rely on the slope of the ECG and lines between the S-peak and T-peak. Such algorithms have long computation times and are prone to errors from electronic noise, artifacts, and physiological changes of the patient.

Figure 1:
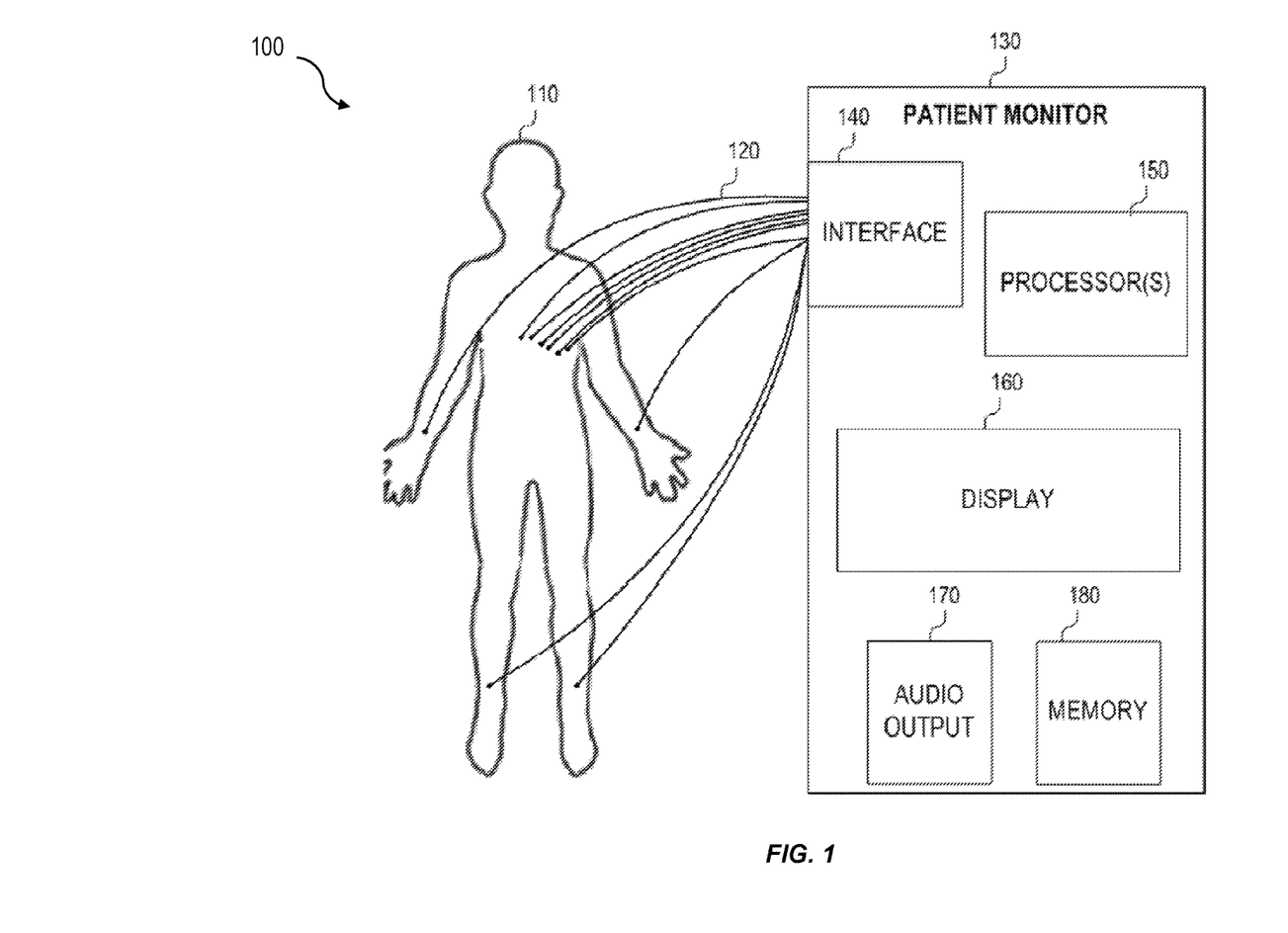
FIG. 1 is a diagram illustrating a patient monitor coupled to an electrocardiogram (ECG) electrode set affixed to a patient.

FIG. 1 is a diagram 100 illustrating an example implementation in which electrocardiogram (ECG) data from a patient 110 is measured by a patient monitor 130. The patient monitor 130 can include memory 180 for storing instructions for execution by one or more processor/processor cores 150. Memory 180 can also be capable of storing data. The patient monitor 130 can include an electronic display 160 for rendering visual information that corresponds to the ECG data and patient vital signs (e.g., values, cardiac cycle waveforms, etc.) as well as visual alerts of ECG abnormalities/conditions. In addition, the patient monitor 130 can also include an interface 140 that permits for wired or wireless communication with one or more electrodes of an ECG electrode set 120 affixed to the patient 110 and/or a remote medical device and/or a remote computing system or network to transmit/receive data pertaining to ECG data and the like. Multiple interfaces 140 can be used in some variations. The patient monitor 130 can implement the processing described herein and, in other variations, the patient monitor 130 can transmit data characterizing the ECG data of the patient 110 to a remote computing system (e.g., medical device, back-end computing system, etc.) via the interface 140 for a remote generation of an ECG signal. Upon detection of an abnormal event based on the signal generation described herein, an audible alarm can also sound from an audio output 170 alerting a patient and/or medical staff.

Figure 2:
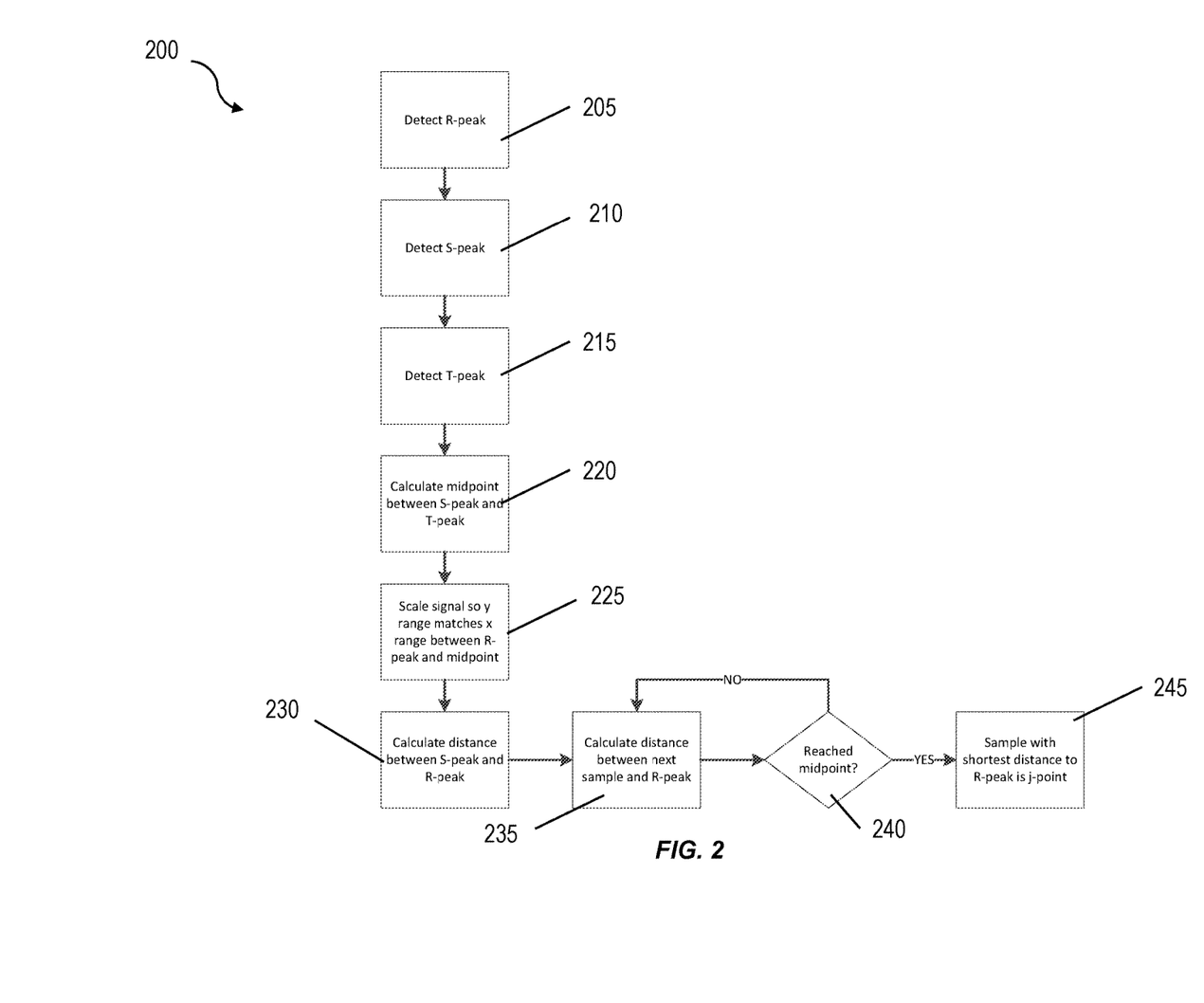
FIG. 2 is a process flow diagram illustrating an algorithm that determines the location of the J-point.

FIG. 2 is a process flow diagram illustrating an algorithm 200 that can determine the location of the J-point in an ECG signal, for example, by using data derived from the ECG electrode set (sometimes referred to herein as ECG data or ECG signal). Such data can include, for example, a series of discrete samples that, in turn, form concatenated cardiac cycle waveforms that each correspond to a single heartbeat.

Figure 3:
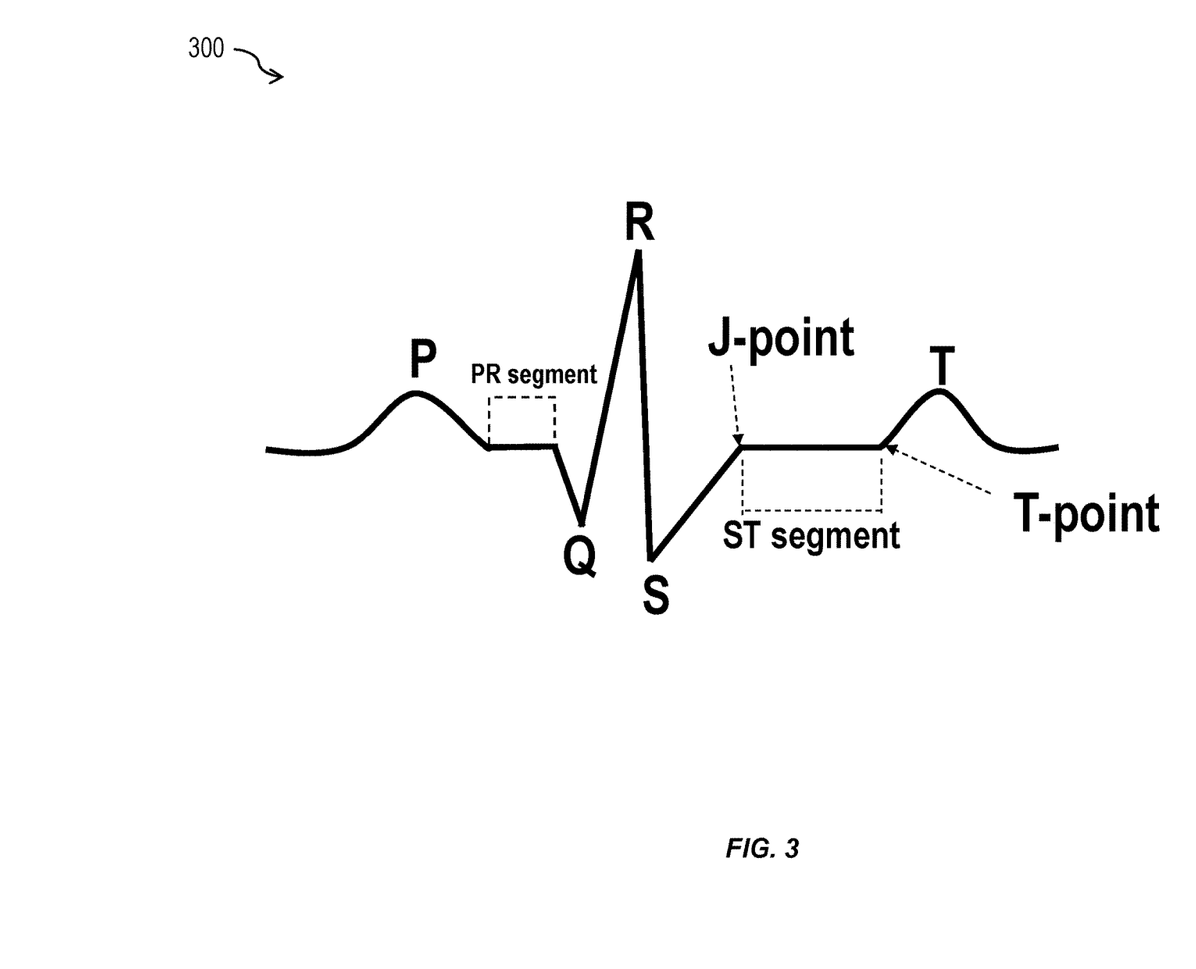
FIG. 3 is a plot of an example cardiac cycle waveform showing the Q, R, S, and T waves, the J-point, and the ST segment.

With reference to waveform 300 of FIG. 3, each cardiac cycle waveform can have a QRS complex and an R-peak, S-peak, T-peak, J-point, and an ST segment. The QRS complex characterizes the depolarization of the right and left ventricles of the human heart. The ST segment characterizes an interval between ventricular depolarization and repolarization and occurs after the QRS complex. The ST segment corresponds to a line on an electrocardiogram that begins with the end of the QRS complex and ends at the beginning of the T wave (i.e., repolarization). The height of the ST segment is normally equal to that of the PR segment and/or the TP segment (sometimes referred to herein as a baseline relative to which deviation of the ST segment is measured). ST segment elevation can be found in patients with acute myocardial infarction and other conditions while ST segment depression is an indicator of coronary ischemia. The TP segment of a cardiac cycle waveform is the segment defined by the end of the T wave and start of a next P wave in the cardiac cycle waveform. The PR segment of a cardiac cycle waveform is the segment defined by an end of a P wave and start of a QRS complex in the cardiac cycle waveform.

The algorithm 200 can, in some implementations, be performed by the patient monitor 130. In addition or in the alternative, the locating of the J-point can be performed by a computing device remote from the patient monitor 130.

At 205, 210, and 215, the R-peak, S-peak, and T-peak are located for a cardiac cycle waveform. Such location can be performed, for example, by taking a first or second derivative of the cardiac cycle waveform (or portion thereof) and/or by using Fourier or wavelet transforms. The R-peak, for example, can be located by searching an interval (e.g., 60 milliseconds, etc.) before and after a QRS detection mark for a point of maximal value. The S-peak, for example, can be located by taking a second derivative of at least a portion of the cardiac cycle waveform and identifying the first inflection point after the R-peak. The T-peak, for example, can be located by determining a maximal absolute value, relative to the isoelectric line, between the R-peak and the R-peak plus an interval (e.g., 400 milliseconds, etc.).

At 220, a midpoint between the S-peak and T-peak can be calculated. The midpoint represents the sample corresponding to a time value that is halfway between the respective time values of the S-peak and the T-peak.

The algorithm 200 can continue by searching for the signal sample closest to the R-peak in a window (i.e., a subset of the samples forming the cardiac cycle waveform) between the S-peak and the midpoint. To effect such searching, the ECG signal (or a portion thereof) can, at 225, be scaled. Such scaling can include applying a weight given to changes in distance in both the x direction (on the x-axis representing time) and y direction (on the y-axis representing voltage value). This scaling, can for example, be such that it is equally applied in both directions. In order to accomplish this, the x and y axis can be scaled at 225 so both cover a distance from 0 to 100 units in the window from the R-peak to the midpoint. The y values of samples can be multiplied by a number so the R-peak is at 100 and the S-peak is at 0 (e.g., the R-peak and S-peak can be normalized to 100 and 0, respectively). The x values of samples are multiplied by a number so the R-peak is at 0 and the midpoint is at 100.

Figure 12:
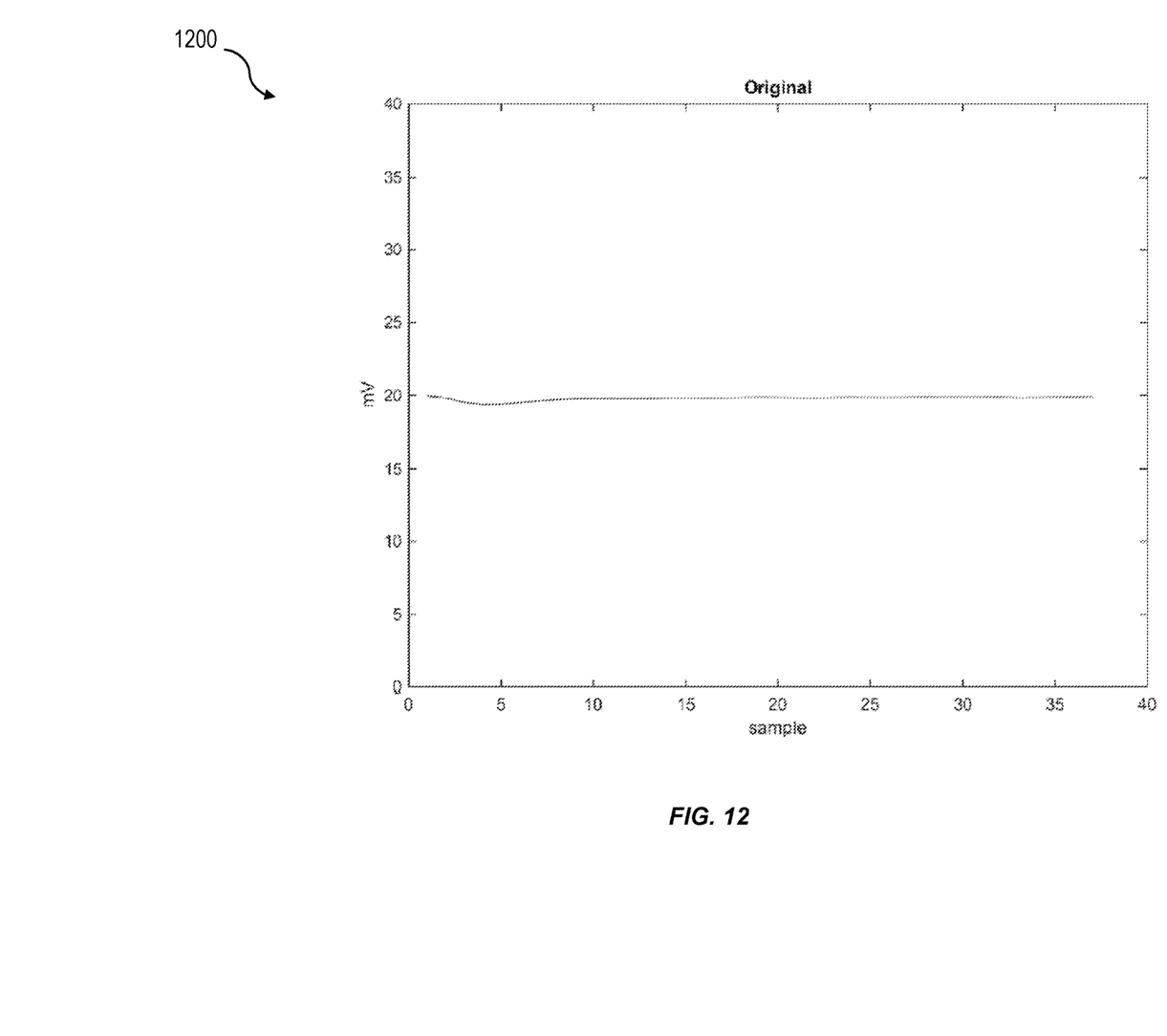
FIG. 12 is a plot showing an example ECG signal before scaling.
Figure 13:
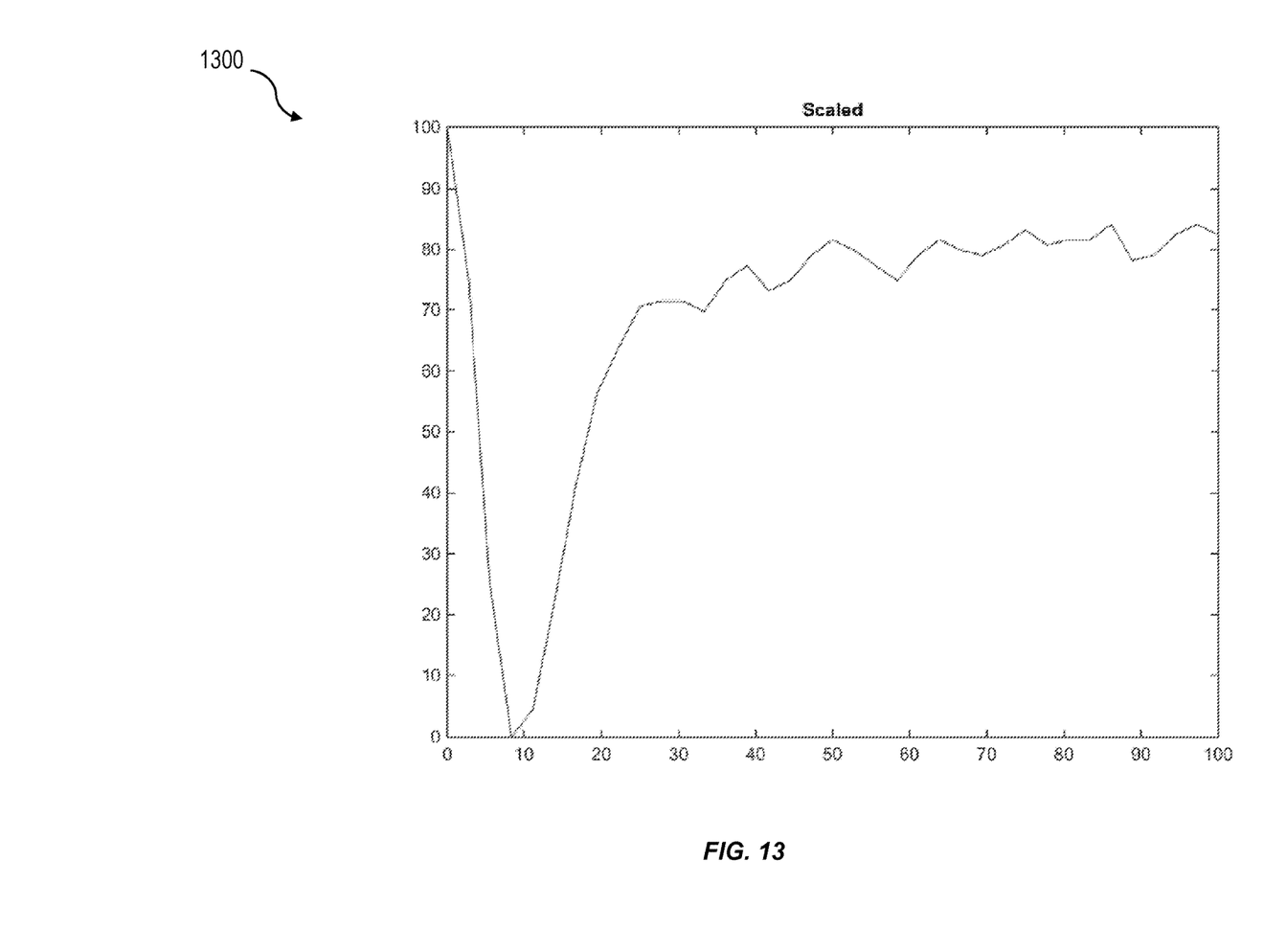
FIG. 13 is a plot showing the example signal of FIG. 12 after scaling, so both the x and y ranges are 100.

FIG. 12 is a plot 1200 of millivolts (mV) versus sample number (e.g., time) and shows an example ECG signal before scaling. FIG. 13 is a plot 1300 of the example ECG signal as a function of sample number and shows the example signal of FIG. 12 after scaling, so both the x and y ranges are 100. As can be seen, the features of the cardiac cycle waveform become much more apparent after scaling.

Figure 4:
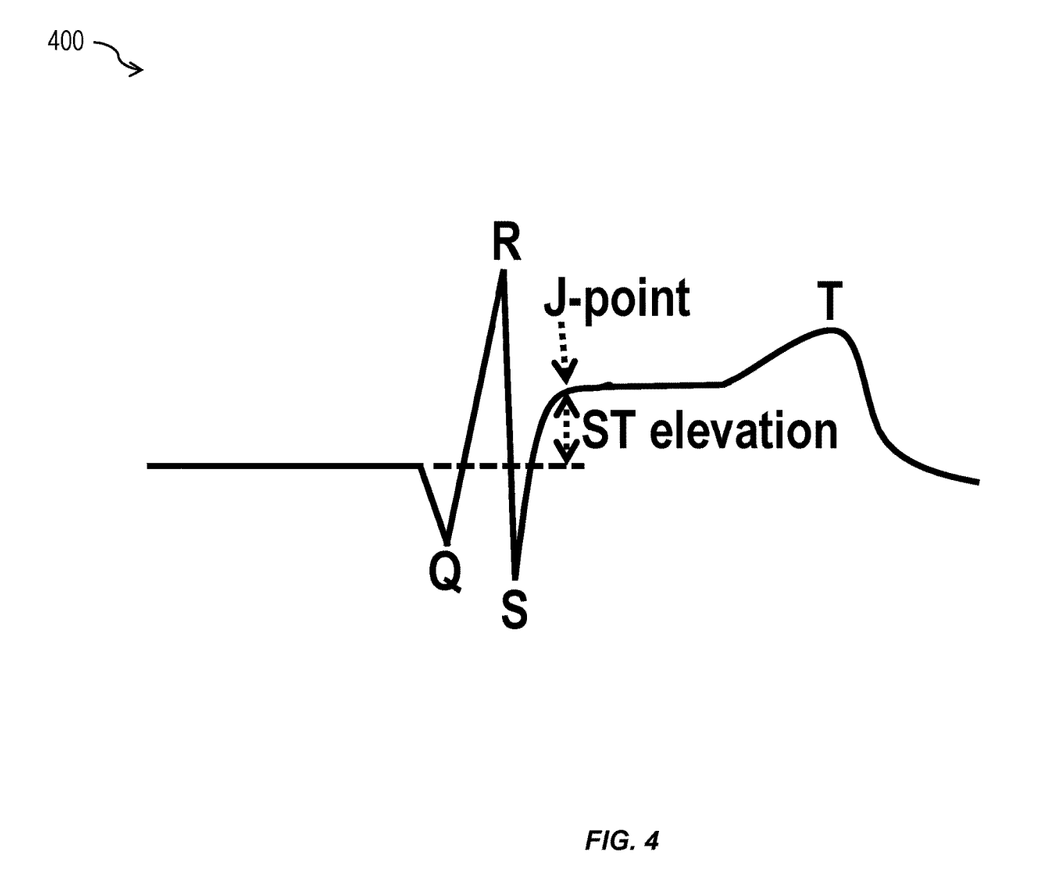
FIG. 4 is a plot of an example cardiac cycle waveform showing ST elevation.

The algorithm 200 can continue, at 230, by calculating the distance of samples, $\Delta d$, between each sample and the R-peak. The distance can be, for example, the Euclidean distance between the coordinates of the sample (along the x and y axes) and the coordinates of the R-peak (along the x and y axes) in which $\Delta d = \sqrt{(x2-x1)^2 + (y2-y1)^2}$, where (x1, y1) are the x-y coordinates of the R-peak and (x2, y2) are the x-y coordinates of the sample. Other methods of determining distance can also be utilized. The samples can be selected in various manners including by starting with the sample near the S-peak. The algorithm 200 then examines a next adjacent sample within the window, at 235, moving toward the midpoint between the S-peak and T-peak, and calculates the distance, $\Delta d$, between such sample and the R-peak. The algorithm 200 can continue and examines the next adjacent samples while determining at 240 whether the midpoint is reached. When the midpoint is reached, at 245, the sample with the shortest distance, $\Delta d$, to the R-peak is selected as the J-point. The J-point can, in turn, be used to determine ST segment deviation (e.g., elevation or depression in relation to a baseline) (such as that illustrated in waveform 400 of FIG. 4) and/or to determine other cardiac conditions of the patient being monitored.

The algorithm 200 can be applied to the ECG data as it is being generated by the electrode set 120 and/or it can be applied to historically generated ECG data.

Figure 5:
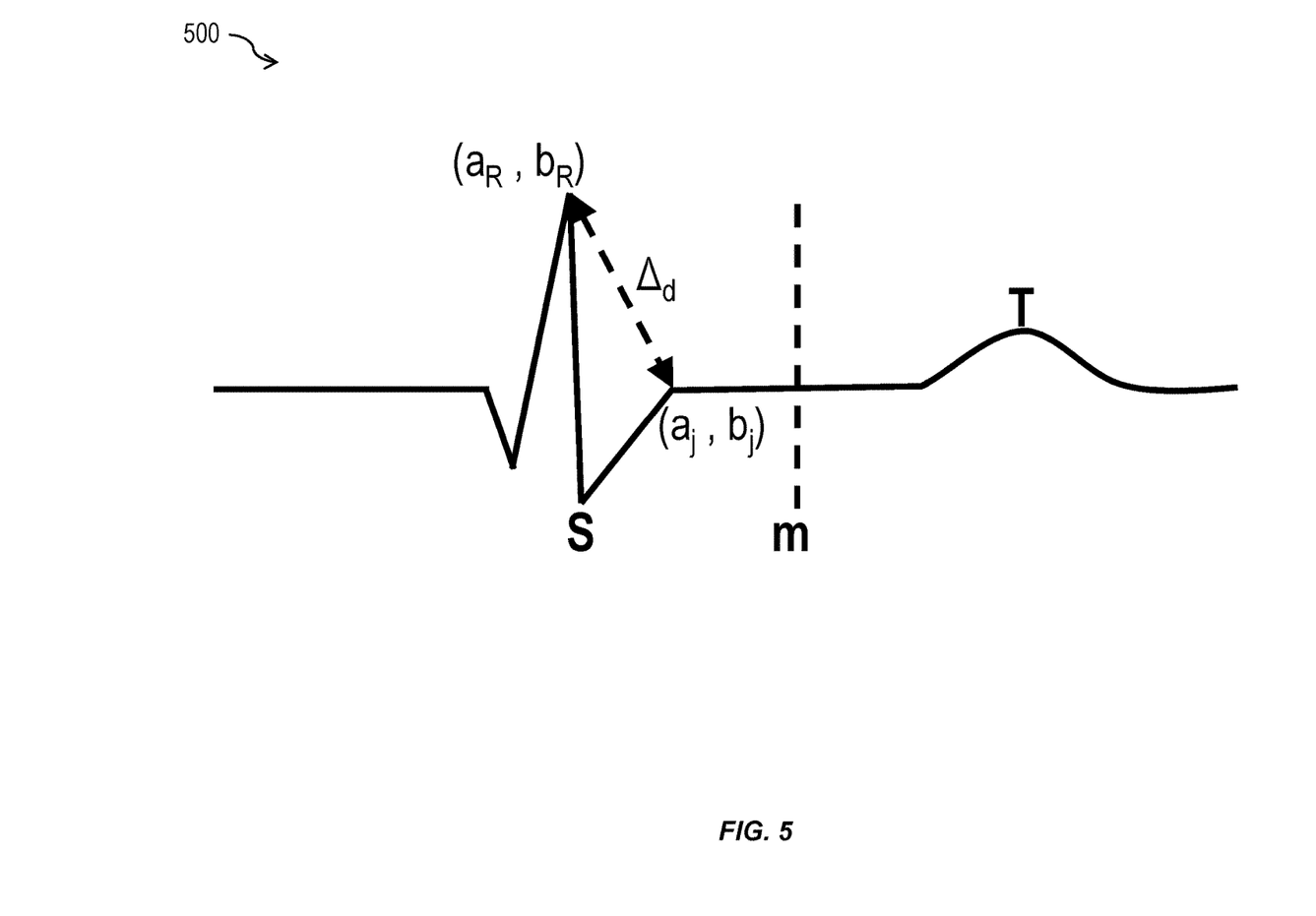
FIG. 5 is a plot of an example cardiac cycle waveform showing normal T-wave morphology.
Figure 6:
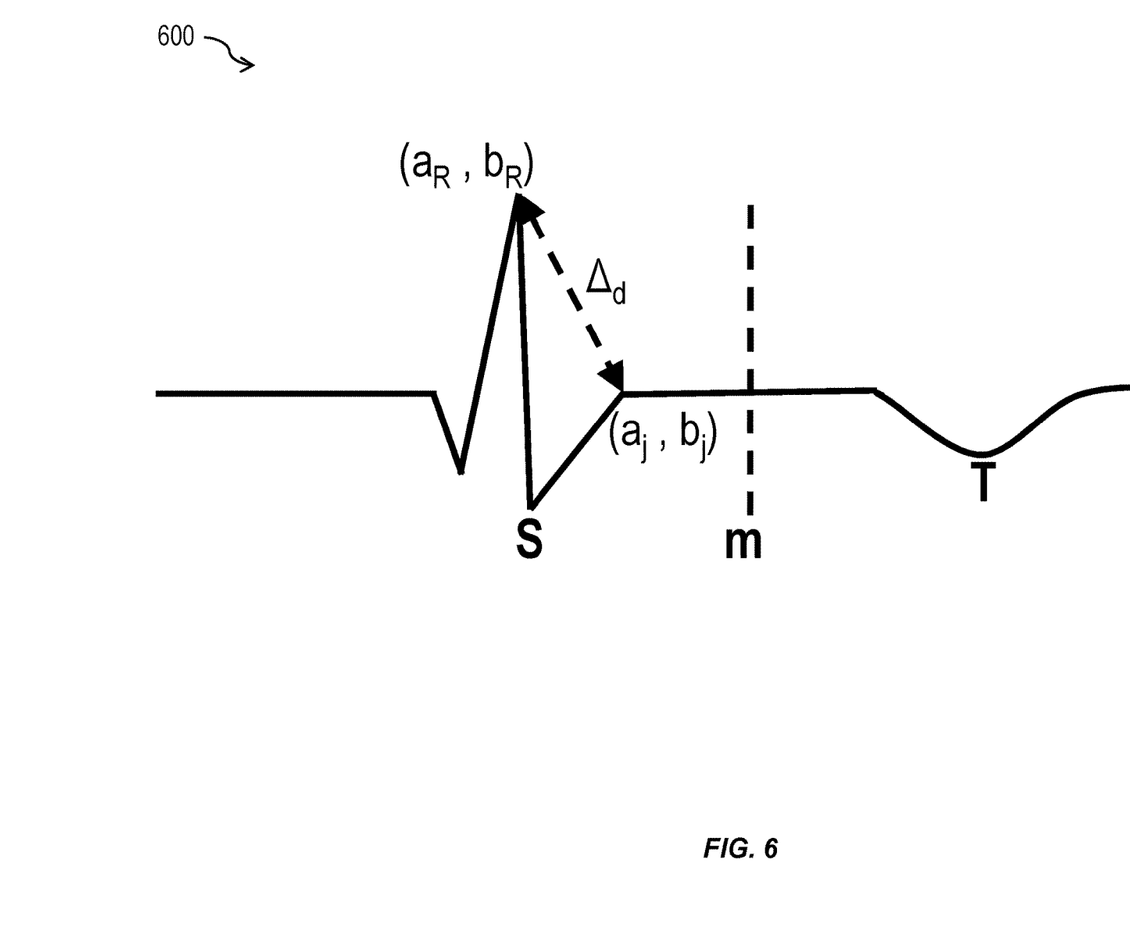
FIG. 6 is a plot of an example cardiac cycle waveform showing inverted T-wave morphology.
Figure 7:
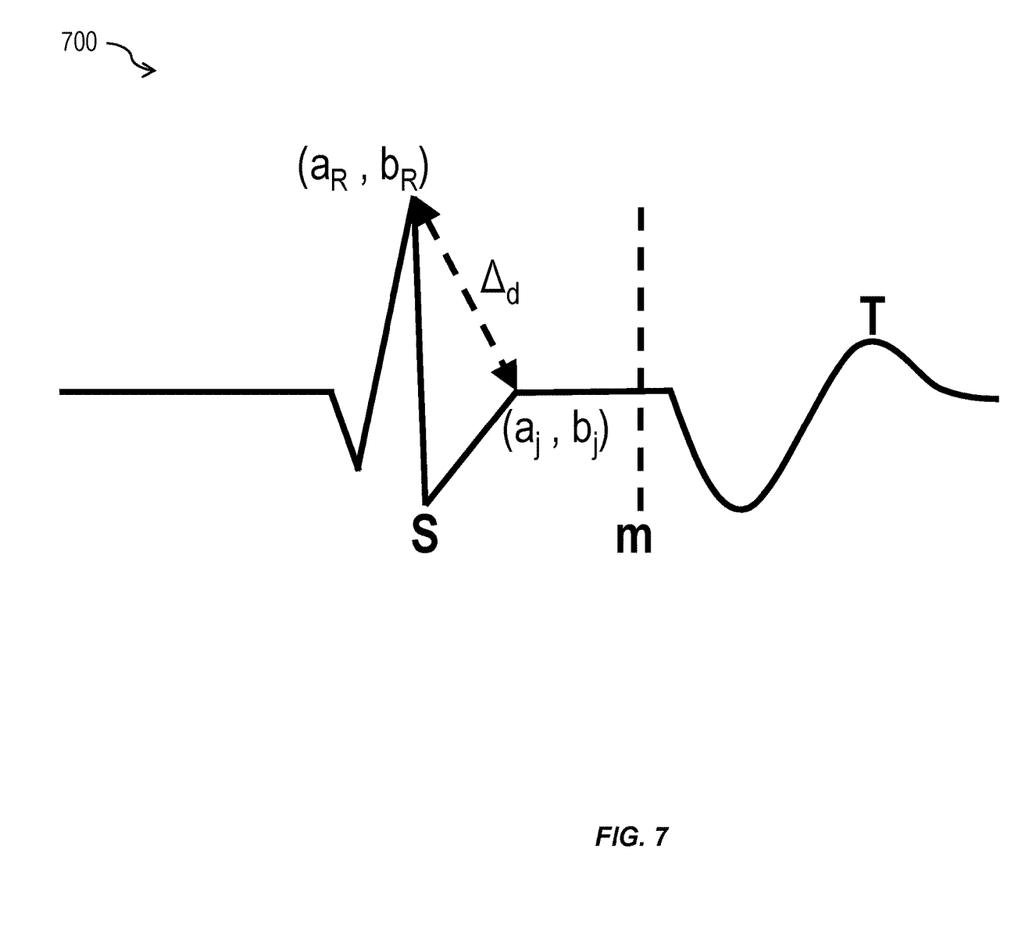
FIG. 7 is a plot of an example cardiac cycle waveform showing biphasic negative/positive T-wave morphology.
Figure 8:
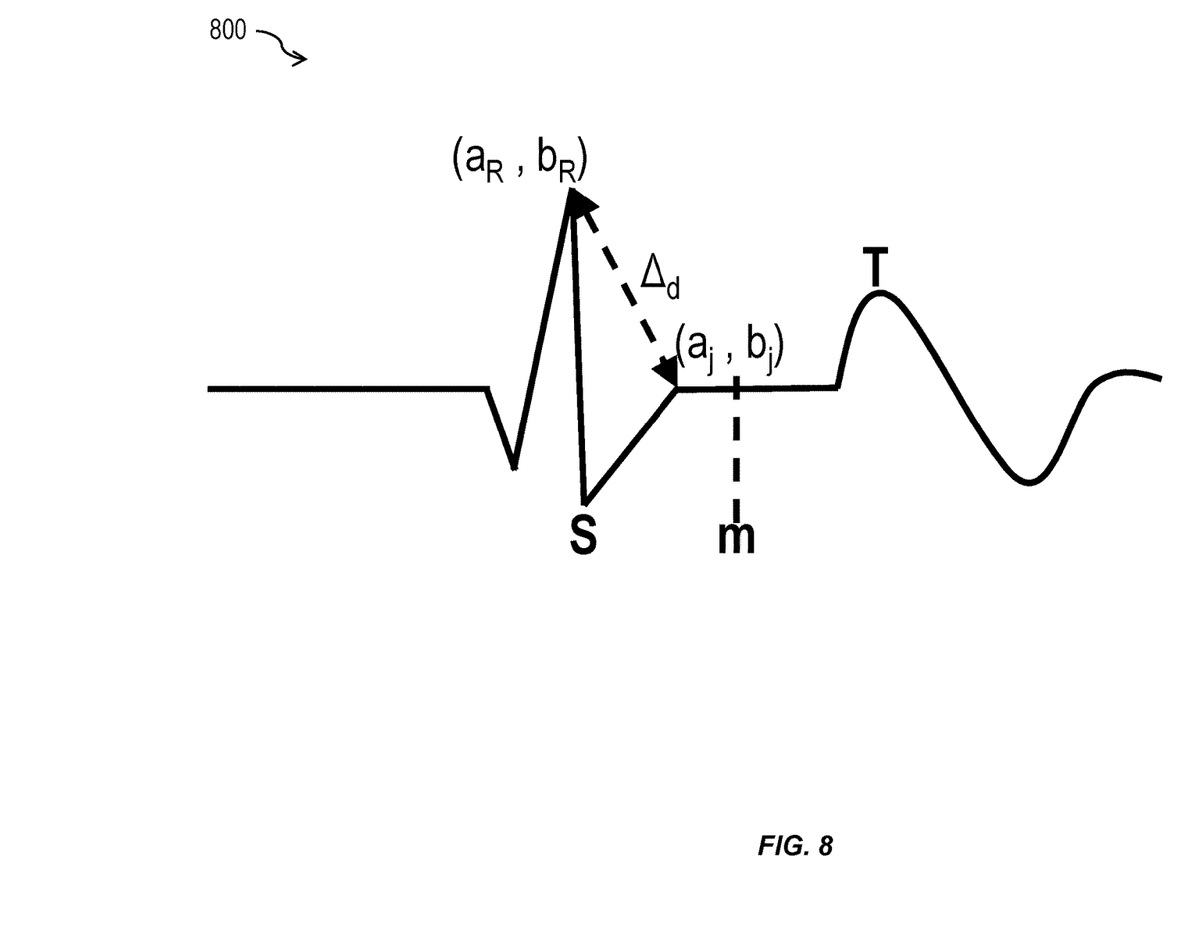
FIG. 8 is a plot of an example cardiac cycle waveform showing biphasic positive/negative T-wave morphology.
Figure 9:
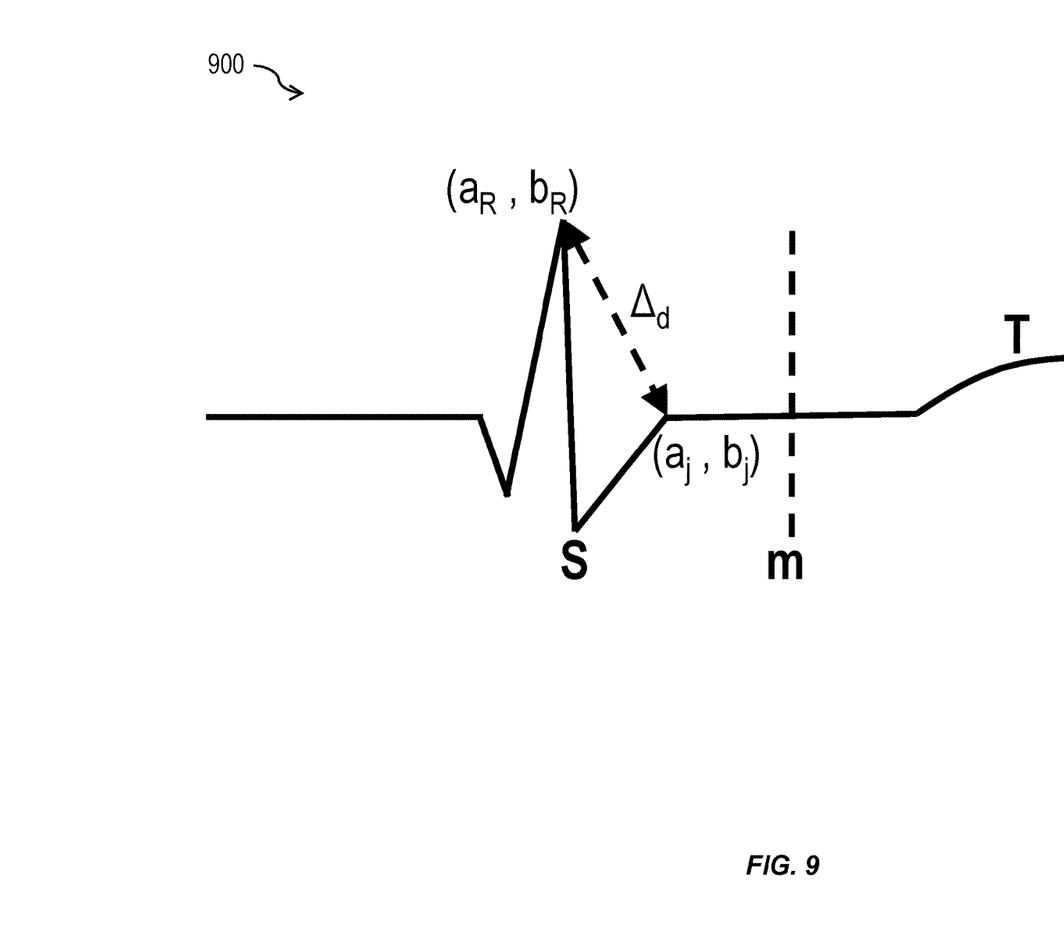
FIG. 9 is a plot of an example cardiac cycle waveform showing increasing T-wave morphology.
Figure 10:
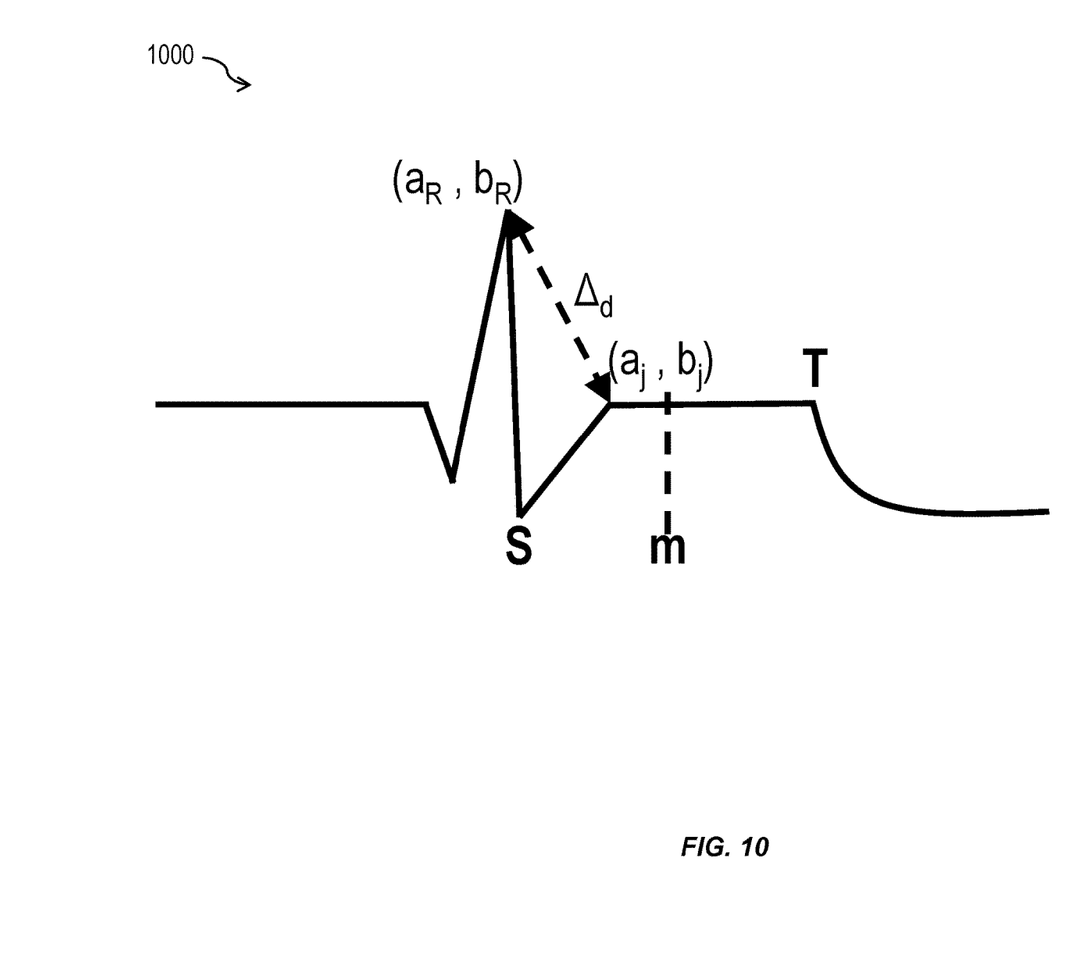
FIG. 10 is a plot of an example cardiac cycle waveform showing decreasing T-wave morphology.

In some implementations, the algorithm 200 can handle different forms of T-wave morphology. For example, different forms of T-wave morphology are shown in waveform 500 of FIG. 5 (normal), waveform 600 of FIG. 6 (inverted), waveform 700 of FIG. 7 (biphasic _/+), waveform 800 of FIG. 8 (biphasic +/_), waveform 900 of FIG. 9 (increasing), and waveform 1000 of FIG. 10 (decreasing). In each case, the algorithm 200 can still operate and identify the J-point given the location of the T-wave peak and the midpoint between the T-wave peak and S-peak.

Figure 11:
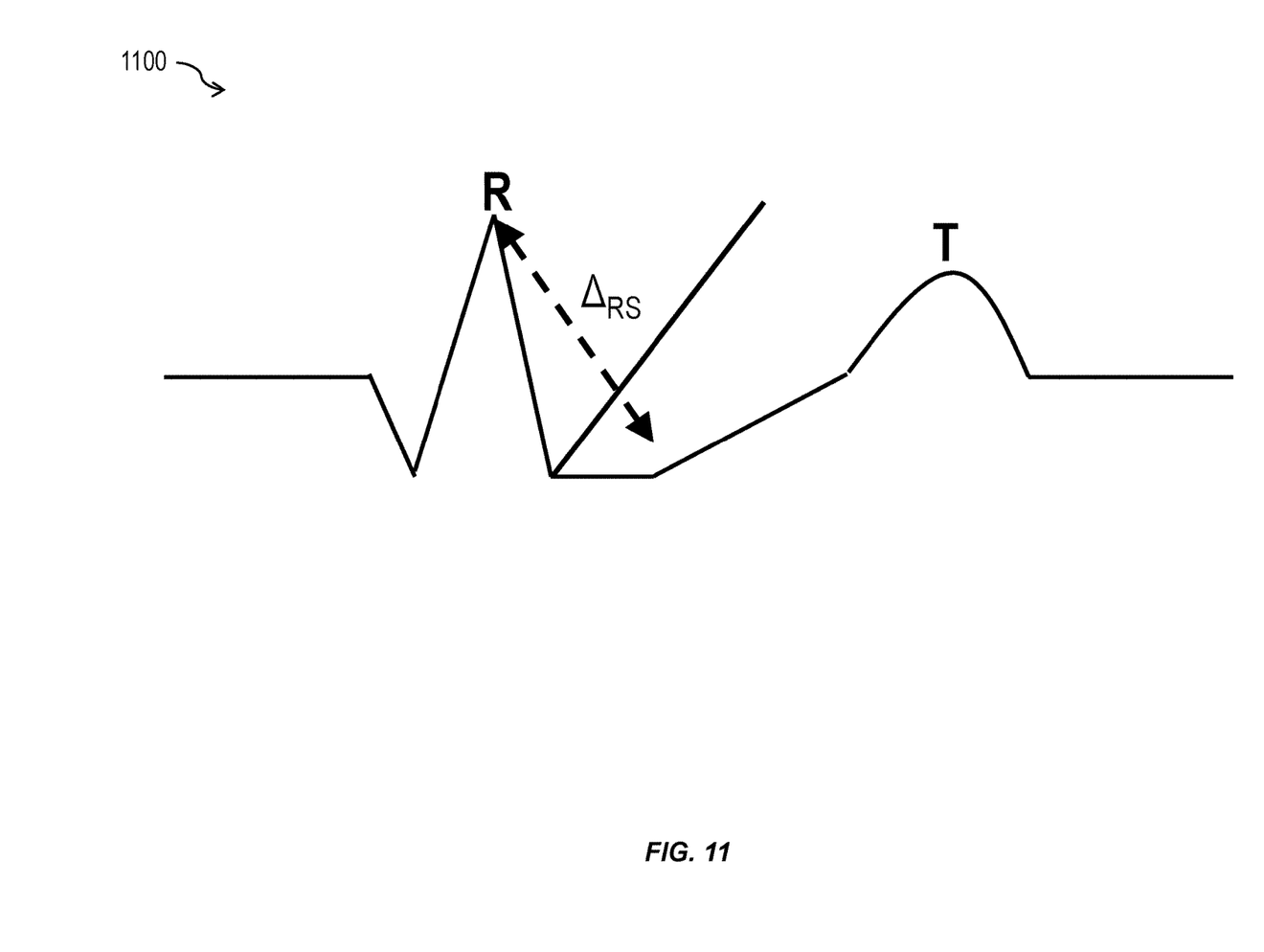
FIG. 11 is a plot of an example cardiac cycle waveform where the S-peak is the closest point to the R-peak.

FIG. 11 is a diagram 1100 that illustrates an example ECG signal where the S-peak is the closest point to the R-peak. In this case, the current subject matter still results in correct/accurate performance and locating of the J-point. In the example, the algorithm 200 chooses the S-peak as the J-point, which provides the correct ST segment elevation for this example.

Although a few variations have been described in detail above, other modifications or additions are possible. For example, other implementations include modifying which samples are examined (i.e., the order and/or selection of samples within the window of the cardiac cycle waveform). For instance, samples within a window of samples from the S-peak to the T-peak can be examined. In addition, the order in which samples are examined can vary. Samples near the midpoint between the S-peak and T-peak can be examined first (i.e., reverse sequential temporal order as opposed to sequential temporal order based on when the samples were measured). Samples can be examined out of order; e.g., the selection of the next sample to be examined can be based on previous examined samples' characteristics, such as but not limited to distance to R-peak and/or slope. As another example, if the previous sample is far away from the R-peak (e.g., separated by a predetermined distance), several samples can be skipped over before examining a sample (e.g., the current subject matter may not compute a distance for every sample in the time series but rather may "skip" over some samples). On the other hand, if the distance to the R-peak is small, the immediate next sample can be examined. The threshold for stopping can be set at a fixed value (e.g., predetermined). Other implementations are possible to effect more rapid and/or efficient detection of the closest sample to the R-peak (which in turn utilizes less computing resources).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a an electronic display, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method for locating a J-point in a cardiac cycle waveform, the method being implemented by one or more data processors forming part of at least one computing device, the method comprising:
   receiving electrocardiogram (ECG) data derived from an ECG electrode set affixed to a patient, the ECG data comprising a sequence of cardiac cycle waveforms that each correspond to a single cardiac cycle, each waveform comprising a series of samples;
   locating, for each cardiac cycle waveform, an R-peak, an S-peak, and a T-peak;
   calculating, for each cardiac cycle waveform, a Euclidian distance between the R-Peak and each of a plurality of samples within a window of samples;
   locating a J-point for each cardiac cycle waveform by identifying, as a location of the J-point in the cardiac cycle waveform, a sample from among the plurality of samples having the shortest Euclidian distance to the R-peak; and
   determining a physical state of the patient based on the J-point located in at least one cardiac cycle waveform.

2. The method of claim 1, further comprising:
   calculating, for each cardiac cycle waveform, a midpoint sample between the S-peak and the T-peak;
   wherein the window only includes samples between the S-peak and the midpoint sample.

3. The method of claim 1, further comprising:
   identifying, for each cardiac cycle waveform, beginning of a T wave corresponding to the T-peak; and
   measuring, for each cardiac cycle waveform, a deviation of an ST segment starting at the J-point and terminating at the beginning of the T wave relative to a baseline, the ST segment corresponding to an interval between ventricular depolarization and repolarization of the patient.

4. The method of claim 3, wherein the baseline is a PR interval of the corresponding cardiac cycle waveform defined by an end of a P wave and start of a QRS complex in the cardiac cycle waveform.

5. The method of claim 3, further comprising:
providing data characterizing the measured deviation of the ST segment.

6. The method of claim 5, wherein providing data characterizing the measured deviation of the ST segment comprises at least one of: displaying at least a portion of the data on an electronic display, loading at least a portion of the data into memory, storing at least a portion of the data into persistent storage, or transmitting at least a portion of the data to a remote computing system.

7. The method of claim 3, wherein the measured deviation is an elevation of the ST segment relative to the baseline or a depression of the ST segment relative to the baseline.

8. The method of claim 1 further comprising:
scaling, prior to the calculating, each cardiac cycle waveform to a predetermined scale.

9. The method of claim 8, wherein each cardiac cycle waveform is scaled such that, on an x-axis of the cardiac cycle waveform, the scaling is between the R-peak and a midpoint sample between the S-peak and the T-peak and, on a y-axis of the cardiac cycle waveform, the scaling is between.

10. The method of claim 1, further comprising:
providing, for each cardiac cycle waveform, data specifying the location of the identified J-point for the cardiac cycle waveform,
wherein the providing data comprises at least one of:
displaying at least a portion of the data on an electronic display, loading at least a portion of the data into memory, storing at least a portion of the data into persistent storage, or transmitting at least a portion of the data to a remote computing system.

11. The method of claim 1, wherein at least one of the receiving, the locating the R-peak, the S-peak, and the T-peak, the calculating, the locating the J-point, and the determining is executed by a patient monitor in communication with the ECG electrode set.

12. The method of claim 1, wherein the ECG data is continuously updated while the patient is being monitored.

13. The method of claim 1, wherein in the calculating, the Euclidian distance between the R-Peak and each of the plurality of samples is calculated using the following equation:

$$d=\sqrt{(x_2-x_1)^2++(y_2-y_1)^2}$$

where d is the Euclidian distance,
$(x_1, y_1)$ are coordinates of the R-peak, and
$(x_2, y_2)$ are coordinates of the sample.

14. A system for locating a J-point in a cardiac cycle waveform, the system comprising:
at least one data processor; and
memory storing instructions which, when executed by the at least one data processor, perform operations comprising:
receiving electrocardiogram (ECG) data derived from an ECG electrode set affixed to a patient, the ECG data comprising a sequence of cardiac cycle waveforms that each correspond to a single cardiac cycle, each waveform comprising a series of samples;
locating, for each cardiac cycle waveform, an R-peak, an S-peak, and a T-peak;
calculating, for each cardiac cycle waveform, a Euclidian distance between the R-Peak and each of a plurality of samples within a window of samples;
locating a J-point for each cardiac cycle waveform by identifying, as a location of the J-point in the cardiac cycle waveform, a sample from among the plurality of samples having the shortest Euclidian distance to the R-peak; and
determining a physical state of the patient based on the J-point located in at least one cardiac cycle waveform.

15. The system of claim 14 further comprising:
an electrocardiogram (ECG) electrode set for generating ECG signals when affixed to a patient.

16. The system of claim 15, wherein the at least one data processor and memory form part of a patient monitor, the patient monitor comprising an interface for communication with the ECG electrode set.

17. A non-transitory computer program product storing instructions which, when executed by at least one data processor forming part of at least one computing device, perform operations for locating a J-point in a cardiac cycle waveform, the operations comprising:
receiving electrocardiogram (ECG) data derived from an ECG electrode set affixed to a patient, the ECG data comprising a sequence of cardiac cycle waveforms that each correspond to a single cardiac cycle, each waveform comprising a series of samples;
locating, for each cardiac cycle waveform, an R-peak, an S-peak, and a T-peak;
calculating, for each cardiac cycle waveform, a Euclidian distance between the R-Peak and each of a plurality of samples within a window of samples;
locating a J-point for each cardiac cycle waveform by identifying, as a location of the J-point in the cardiac cycle waveform, a sample from among the plurality of samples having the shortest Euclidian distance to the R-peak; and
determining a physical state of the patient based on the J-point located in at least one cardiac cycle waveform.

* * * * *